United States Patent [19]

Lietz

[11] Patent Number: 4,474,986
[45] Date of Patent: Oct. 2, 1984

[54] PREPARATION OF PROPAFENONE

[75] Inventor: Helmut Lietz, Neustadt, Fed. Rep. of Germany

[73] Assignee: BASF Aktiengesellschaft, Fed. Rep. of Germany

[21] Appl. No.: 476,575

[22] Filed: Mar. 18, 1983

[30] Foreign Application Priority Data

Mar. 19, 1982 [DE] Fed. Rep. of Germany ....... 3210061

[51] Int. Cl.$^3$ ............................................. C07C 85/00
[52] U.S. Cl. .................................................. 564/349
[58] Field of Search ......................................... 564/349

[56] References Cited

U.S. PATENT DOCUMENTS 3,178,420 4/1965 Palopoli et al. ................ 564/349 X
3,542,872 11/1970 Koppe et al. ..................... 564/349
3,864,390 2/1975 Le Count et al. .............. 564/349 X
3,876,802 4/1975 Brändström et al. ........... 564/349 X

FOREIGN PATENT DOCUMENTS 2001431 5/1974 Fed. Rep. of Germany ...... 564/349

Primary Examiner—Paul F. Shaver
Attorney, Agent, or Firm—Keil & Witherspoon

[57] ABSTRACT

A process for the preparation of propafenone wherein
1. 2'-hydroxyacetophenone is reacted with epichlorohydrin,
2. the resulting 2-(2',3'-epoxypropoxy)-acetophenone is reacted with propylamine,
3. the resulting 2-(2'-hydroxy-3'-propylaminopropoxy)-acetophenone is reacted with benzaldehyde, accompanied by elimination of water, and
4. the resulting 2-(2'-hydroxy-3'-propylaminopropoxy)-benzalacetophenone is hydrogenated.

1 Claim, No Drawings

PREPARATION OF PROPAFENONE

The invention relates to a novel process for the preparation of propafenone.

Propafenone (2'-(2-hydroxy-3-propylaminopropoxy)-3-phenylpropiophenone hydrochloride, German Pat. No. 2,001,431) is a substance having an anti-arrhythmic action. According to the said German patent, it is obtained by reacting 2-hydroxy-omega-phenylpropiophenone (as the sodium salt) with 1-chloro-2,3-epoxypropane and then reacting the resulting 2-(2',3'-epoxypropyl)-omega-phenylpropiophenone with n-propylamine and converting the product to the hydrochloride. This process gives a yield of only about 66%. Moreover, the starting material (2-hydroxy-omega-phenylpropiophenone) required for the reaction can only be obtained with difficulty from 2-hydroxyacetophenone by condensing with benzaldehyde and then hydrogenating the reaction product.

The present invention provides a process for the preparation of propafenone, wherein
1. 2'-hydroxyacetophenone is reacted with epichlorohydrin,
2. the resulting 2-(2',3'-epoxypropoxy)-acetophenone is reacted with propylamine,
3. the resulting 2-(2'-hydroxy-3'-propylaminopropoxy)-acetophenone is reacted with benzaldehyde, accompanied by elimination of water, and
4. the resulting 2-(2'-hydroxy-3'-propylaminopropoxy)-benzalacetophenone is hydrogenated.

The first reaction step is as a rule carried out in epichlorohydrin as the solvent. However, it is also possible to dissolve the epichlorohydrin in a different solvent, such as toluene or acetone, and to employ it in a slight excess (a molar ratio of from 1:1 to 2:1). The reaction is advantageously carried out at 50°–150° C., preferably at the boiling point of the solvent used, in the presence of a base, such as sodium hydroxide or potassium carbonate. The product of the first reaction step does not have to be specially purified for the next stage. It is not necessary to isolate the sodium salt of 2'-hydroxy-acetophenone.

The second stage is carried out by adding the substances mentioned and refluxing the mixture for several hours. Advantageously, propylamine is used as the solvent, but alcohols (isopropanol and ethanol) may also be used. For further processing, the reaction product obtained is converted to a salt, for example the hydrochloride or oxalate. The oxalate has proved particularly advantageous. This conversion is advantageously carried out in alcoholic solution.

Elimination of water and reaction with benzaldehyde in the 3rd stage are carried out in a solvent, such as an aqueous lower alcohol, in the presence of a base, such as sodium hydroxide or potassium hydroxide, at 50°–150° C., preferably at the boiling point of the solvent.

The product obtained in stage 3 is used direct for the hydrogenation in stage 4. For this purpose, further solvent and a catalyst, such as palladium/charcoal or Raney nickel are added and the calculated amount, or a slight excess, of hydrogen is passed in. The hydrogenation is as a rule carried out at room temperature.

From the reaction solution thus obtained, the propafenone can be isolated after it has been converted to a salt. Suitable acids for forming such a salt include the hydrohalic acids, oxalic acid and tartaric acid, hydrochloric acid being preferred.

The novel process has the following advantages:
1. It gives very pure propafenone.
2. It is easy to carry out. The intermediates as a rule do not have to be isolated in a pure form, contrary to what is necessary in the conventional processes.
3. For the reaction of the 2'-hydroxyacetophenone with the epichlorohydrin, it is not necessary to employ the sodium salt of the former. Instead, 2'-hydroxyacetophenone can be employed direct.
4. The process gives a substantially better yield of propafenone, based on 2'-hydroxyacetophenone employed. In the conventional process, the yield is about 45%, whilst in the novel process it is, overall, 55%.

EXAMPLE

Stage 1

Preparation of 2-(2',3'-epoxypropoxy)-acetophenone 27.2 g of 2'-hydroxyacetophenone and 8 g of sodium hydroxide were suspended in 200 ml of epichlorohydrin. The yellowish white suspension was refluxed for 4 hours and cooled, and the crystals were filtered off. The filtrate was concentrated. The residue, 38.8 g=180.9 millimoles (90.5%, based on 2'-hydroxyacetophenone) was employed, without additional purification, for the next stage.

Stage 2

34.8 g of 2-(2',3'-epoxypropoxy)-acetophenone and 150 ml of propylamine were refluxed for 4 hours, with stirring. When the mixture had cooled, the excess propylamine was distilled off. The residue (57.9 g) was dissolved in 100 ml of methanol and 30 g of oxalic acid dissolved in 250 ml of methanol were added to this solution. The mixture was heated, and after it had cooled, the crystals formed (23 g) were filtered off. The filtrate was concentrated. The residue was dissolved in 350 ml of a hot 20/80 methanol/acetone mixture. Overnight, crystals separated out and these were filtered off. The total yield was 52.2 g (84.6%, based on the "epoxide" employed); melting point 159° C.

Stages 3+4

Preparation of propafenone hydrochloride 20 g of 2-(2'-hydroxy-3'-propylaminopropoxy)-acetophenone oxalate were dissolved in 450 ml of hot methanol. 16 g of sodium hydroxide, dissolved in 30 ml of distilled water, and 10.6 g of benzaldehyde were added to this solution and the mixture was refluxed for 4 hours. When it had cooled, 2 g of 10% strength Pd/C and 500 ml of methanol were added. The reaction product was hydrogenated under atmospheric pressure (hydrogen absorption: 1,350 ml). The catalyst was filtered off and thoroughly washed with methanol. The filtrate was concentrated. The residue was dissolved in 500 ml of hot 1 N HCl. On cooling, the solution deposited crystals, which were filtered off (crystals I). The filtrate was rendered alkaline and extracted with 3×70 ml of chloroform. The organic phases were combined and concentrated. The residue was brought to pH 2 with 1 N HCl and again concentrated. This new residue was recrystallized from about 250 ml of an 80/20 acetone/methanol mixture. The resulting crystals (II) were filtered off and dried.

The yield was 14.9 g=39.4 millimoles (12.1 g of crystals I, and 2.8 g of crystals II), amounting to 67.2% of theory based on 2-(2'-hydroxy-3'-propylaminopropoxy)-acetophenone oxalate employed. The hydrochloride melted at 172° C.

We claim:

1. A process for the preparation of propafenone, wherein
   1. 2'-hydroxyacetophenone is reacted with epichlorohydrin,
   2. The resulting 2-(2',3'-epoxypropoxy)-acetophenone is reacted with propylamine,
   3. The resulting 2-(2'-hydroxy-3'-propylaminopropoxy)-acetophenone is reacted with benzaldehyde, accompanied by elimination of water, and
   4. The resulting 2-(2'-hydroxy-3'-propylaminopropoxy)-benzalacetophenone is hydrogenated.

* * * * *